United States Patent [19]

Andrews, Sr.

[11] 4,079,478

[45] Mar. 21, 1978

[54] TONGUE BRUSH

[76] Inventor: Donald O. Andrews, Sr., 1513 Brush Rd., Apt. 89, Akron, Ohio 44306

[21] Appl. No.: 736,723

[22] Filed: Oct. 29, 1976

[51] Int. Cl.² .......................................... A61B 17/24
[52] U.S. Cl. ................................ 15/210 R; 15/22 A; 128/15; 128/304
[58] Field of Search ................ 15/22 A, 26, 160, 201, 15/202, 210 R, 97 R; 128/15, 304

[56] References Cited

U.S. PATENT DOCUMENTS

| 726,716 | 4/1903 | Maher | 15/201 |
|---|---|---|---|
| 1,735,582 | 11/1929 | Meadoff | 15/176 X |
| 1,746,784 | 2/1930 | Lee | 15/176 |
| 1,755,881 | 4/1930 | Kilbride | 15/145 X |
| 2,677,842 | 5/1954 | Sherwin | 15/210 R |
| 3,484,795 | 12/1969 | Nicolay | 15/210 R X |
| 3,736,616 | 6/1973 | Seip | 15/210 R |

FOREIGN PATENT DOCUMENTS

| 496,865 | 11/1919 | France | 15/210 R |
|---|---|---|---|
| 78,410 | 11/1894 | Germany | 15/167 A |
| 7,450 of | 1911 | United Kingdom | 128/15 |
| 13,341 of | 1894 | United Kingdom | 128/304 |

*Primary Examiner*—Daniel Blum
*Attorney, Agent, or Firm*—Reese Taylor

[57] ABSTRACT

A device for cleaning the human tongue is disclosed and includes an elongate handle having a support frame extending from one end thereof and a fibrous cleaning member slidably carried on the support frame. The opposed end of the handle is disposed substantially normal to the longitudinal axis of the handle to form a pistol grip or handle. The cleaning member is carried by the support frame in depending tracks and is slidable along the longitudinal axis of the tool so that when the fibrous cleaning member is brought into contact with the dorsum or top surface of the tongue and either held in place and the tongue moved against it or being moved back and forth against the tongue, the fibrous material is capable of removing foreign matter which might otherwise remain on the surface thereof.

5 Claims, 3 Drawing Figures

TONGUE BRUSH

BACKGROUND OF THE INVENTION

This invention in general relates to devices for improving oral hygiene and, in particular, relates to a brush intended to assist in cleaning the surface of the tongue.

DESCRIPTION OF THE PRIOR ART

At the present time, Applicant is unaware of any existing prior art devices which are in common usage and which would enable the dorsum or top surface of the tongue to be properly cleaned.

In this regard the tongue, and particularly, the top or dorsum surface thereof is generally rough and covered with papillae at least on the anterior or front two-thirds of the area of the tongue. The posterior third of the overall area is somewhat smoother and covered with numerous muciparous glands and lymph follicles.

The papillae which are present in a number of varieties, generally constitute a projection of the mucus membrane and are shaped somewhat like truncated cones with the small end extending downwardly toward the mucus membrane or body of the tongue itself. The follicles are rounded eminences, the center of which is perforated by a minute orifice which leads to a funnel shaped cavity or recess. Additionally, taste buds are scattered over the mucus membrane of the tongue with the tongue being the principal organ of the sense of taste.

The difficulty, from a hygienic standpoint, is that food particles or residue become encrusted on the surface of the tongue and due to the configuration and construction of that surface, the papillae and follicles are natural collecting points for material of this type. This can cause difficulty with regard to unpleasant breath and also can cause sanitary difficulties since food particles trapped by the roughened surface of the tongue will deteriorate in the same manner as food particles between the teeth thereby giving rise to bacterial growth with the obvious attendant undesirable effects thereof.

Accordingly, it becomes desirable to cleanse the tongue to prevent these undesirable effects.

Applicant is aware of a tongue brush and scraper shown in Runnels, U.S. Pat. No. 2,218,072 entitled "Tongue and Brush Scraper" wherein a relatively rigid ribbed typed device is provided for scraping the tongue. Another example of the patent prior art can be seen in British Patent specification No. 17,643 of 1911 issued to Balaban and entitled "Improved Brush or Appliance for Cleaning the Tongue" wherein a soft rubber pad is provided and operates similar to a coarse or rough file. A more recent example of the patent prior art may be seen in Bhaskar, U.S. Pat. No. 3,943,592 for "Tongue Cleaning Device" wherein a piece of tape having high density flexible hooks are secured to the end of a stick.

The present invention is intended to provide a much improved tongue brush capable of confortably, safely and efficiently cleaning the tongue.

SUMMARY OF THE INVENTION

It has been found that the desired cleaning advantages can be obtained by providing a tongue brush essentially comprising an elongate handle, a support frame extending from one end of the handle and a fibrous cleaning member which can be slidably carried by the support frame so that it can be moved back and forth along the axis of the tool against surface of the tongue.

It has been further discovered that the handle can be deformed so as to provide a "pistol grip" for secure grasping by the user to avoid any problems of slipping or inadvertently allowing the entire tool to be slipped inside the mouth.

It has also been discovered that the cleaning member can be provided with a finger engaging appendage to assist in sliding the same relatively of the support frame.

It has also been discovered that by providing a tongue brush of this nature, the surface of the tongue can be relatively easily cleansed by placing the cleaning member against the surface of the tongue and then reciprocating it by means of the finger engaging appendage so that the dorsum or top surface of the tongue is effectively cleansed. It has been discovered that the cleaning member can be a disposable member so that it can be replaced periodically and, being removable, can also be cleaned easily.

It has also been discovered that, if desired, it is possiblie to utilize a small amount of toothpaste or plain water in conjunction with utilization of the tongue brush. However, the primary cleansing action achieved is by means of the brush itself.

Accordingly, production of an improved tongue brush having the above noted characteristics becomes the principal object of this invention with other objects thereof becoming more apparent upon a reading of the following brief specification considered and interpreted in view of the accompanying drawings.

OF THE DRAWINGS

BRIEF DESCRIPTION OF THE PREFERRED EMBODIMENT

Figure 1:
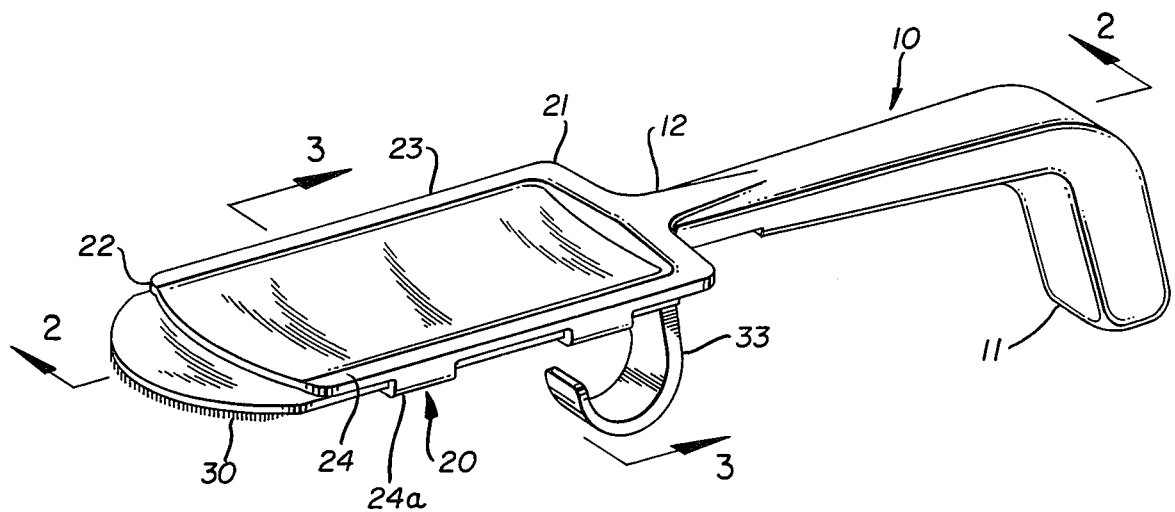
FIG. 1 is a perspective view of the improved tongue brush.
Figure 2:
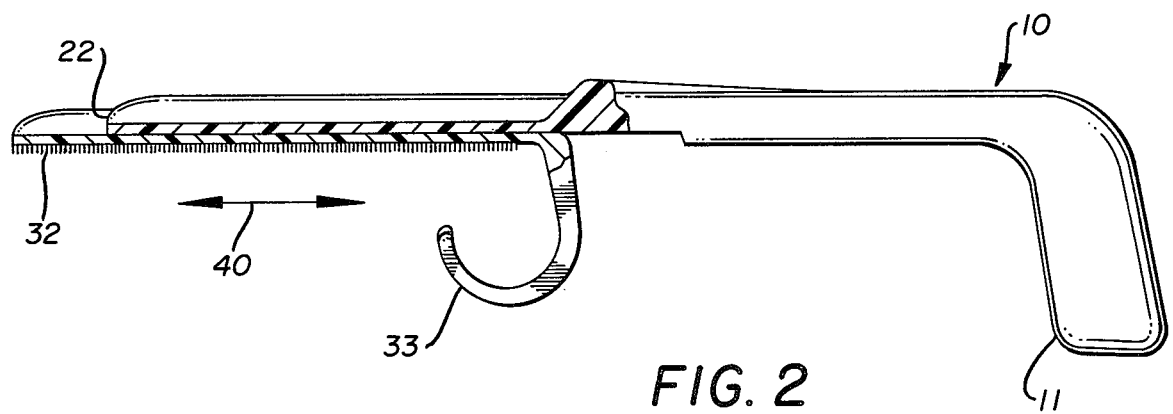
FIG. 2 is a longitudinal sectional view taken along the line 2,2, of FIG. 1.
Figure 3:
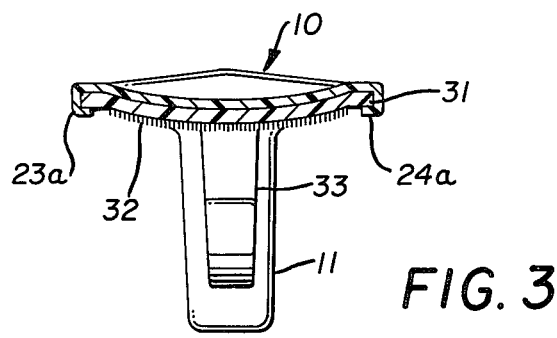
FIG. 3 is a transverse sectional view taken along the line 3,3, of FIG. 1.

Referring, primarily, to FIGS. 1 and 2, it will be noted that the improved tongue brush generally comprises an elongate handle 10 which has support frame 20 extending from one end and which carries a fibrous cleaning member 30.

The handle 10 has a deformed portion at one end 11 which takes the form of what may gnerally be termed to be a pistol grip so that one hand of the user of may grasp it as will be described below.

The opposed end 12 of handle 10 has the support frame 20 extending therefrom either integrally or otherwise.

Support frame 20 takes the form of a rectangular frame having first and second ends 21 and 22 and opposed side frame members 23 and 24. Depending from the side frame member 23 and 24 are track members 23a,24a which are bent back upon themselves so as to form a track for reception of the cleaning member 30.

Cleaning member 30 is essentially a two piece laminante consisting of a layer of flexible material 31 which may be thin gage plastic or similar material as desired and, a fibrous layer 32 which is laminated to one surface of the layer 31.

One end of the flexible layer 31 has an appendage 33 depending therefrom and capable of being engaged by the finger or thumb of the user.

In the form of the invention illustrated herein, the frame has a concave configuration in a transverse fashion for purposes which will be described.

In use or operation and assuming the improved brush to be assembled with the cleaning member 30 slipped into place in the track members 23a, 24a, the pistol grip 11 is grasped by the user and the appendage 33 is engaged by one finger or thumb. In this condition the instrument is placed into the mouth with the fibrous layer 32 of the cleaning member 30 in contact with the dorsum or top surface of the tongue. The cleaning operation can then be achieved in one of two ways.

First, the cleaning member 30 can be moved back and forth across the tongue by means of the finger which engages the appendage 33. Alternatively, the tongue itself can be moved against the cleaning member 30. In either instance, the fibrous layer 32 will contact the papillae and follicles as well as the mucus membrane surface of the tongue thereby removing any foreign material which might be carried thereon.

As noted above, the frame 20 is concave as illustrated for improved contact purposes but it could be planar and the essential operation would remain the same.

Furthermore, it is relatively easy to maintain pressure on the top of the tongue for improved cleaning purposes. Also, the provision of the pistol grip and the curved appendage insures that the overall device will not slip out of the hand during use nor will the cleaning member 30 become disengaged from the overall tool inadvertently.

In this regard, it is contemplated that the cleaning member 30 can be completely removed from the support frame 20 for either cleaning or disposal so that new cleaning members 30 can be substituted.

Accordingly then, a relatively simple, inexpensive yet effective tongue brush has been disclosed herein whereby the desired hygienic results can be achieved.

While a full and complete description of the invention has been set forth in accordance with the dictates of the patent statutes it should be understood that modifications can be resorted to without departing from the spirit hereof or the scope of the appended claims.

In this regard, it will be noted that while no size dimensions have been set forth, the device would normally be relatively small so as to comfortably fit within the mouth of the user without gagging the user.

Furthermore, while plastic has been mentioned as a possible material for the layer 31 of the cleaning member, any material which will provide backing for the fibrous layer 32 and yet retain some flexibility would be approporiate. So far as the material for the handle 10 and frame 20 in the preferred form of the invention, a relatively light weight rigid material such as hard rubber, plastic, etc. would normally be employed but, again, the invention is not intended to be limited to the utilization of any particular structural material.

What is claimed is:

1. A tongue brush, comprising;
    A. an elongated handle having first and second ends,
    B. a support frame having top and bottom surfaces and extending from said first end of said handle and being arcuate in cross-sectional configuration so as to present a convex bottom surface;
    C. an elongated fibrous cleaning member slidably carried by said support frame in contact with and conforming to said convex bottom surface of said support frame, and manual actuating means on the cleaning member for reciprocating the same on the support frame.
2. The brush of claim 1 wherein said handle is deformed adjacent said second end to form a gripping portion disposed substantially normal to the longitudinal axis of said handle.
3. The brush of claim 2 wherein said manual actuating means is a substantially rigid finger engaging appendage projecting from one end of the cleaning member so as to be in longitudinal alignment with said gripping portion of said handle.
4. The brush of claim 1 wherein said cleaning member includes
    A. a flexible backing portion for contact with said convex bottom surface of said frame; and
    B. a fibrous portion attached to the outer surface of said backing portion.
5. The brush of claim 1 wherein
    A. said support frame has a plurality of depending track portions on opposed sides thereof;
    B. said cleaning member being slidably received within said track portions.

* * * * *